US008313522B2

(12) United States Patent
Shin et al.

(10) Patent No.: US 8,313,522 B2
(45) Date of Patent: Nov. 20, 2012

(54) SELF-EXPANDABLE SHAPE MEMORY ALLOY STENT AND METHOD FOR FABRICATING THE SAME

(75) Inventors: Kyong-Min Shin, Seoul (KR); Kang-sun Hong, Seoul (KR)

(73) Assignees: Taewoong Medical Co., Ltd, Kyunggi-do (KR); Kyong-Min Shin, Seoul (KR)

(*) Notice: Subject to any disclaimer, the term of this patent is extended or adjusted under 35 U.S.C. 154(b) by 1067 days.

(21) Appl. No.: 11/474,746

(22) Filed: Jun. 26, 2006

(65) Prior Publication Data

US 2007/0173927 A1 Jul. 26, 2007

(30) Foreign Application Priority Data

Jan. 26, 2006 (KR) .................. 10-2006-0008276

(51) Int. Cl.
*A61F 2/06* (2006.01)

(52) U.S. Cl. .......................... 623/1.2; 623/1.51

(58) Field of Classification Search ............... 623/1.16, 623/1.15, 1.18–1.2, 1.49–1.54, 1.13, 1.35; 264/103; 148/595; 600/36; 29/6.1; 139/454, 139/429–432, 384 R, 408–421; 606/191, 606/192, 194, 198, 108
See application file for complete search history.

(56) References Cited

U.S. PATENT DOCUMENTS

| 6,241,757 | B1* | 6/2001 | An et al. ................. 623/1.1 |
| 2003/0149473 | A1* | 8/2003 | Chouinard et al. ........ 623/1.15 |
| 2004/0236401 | A1* | 11/2004 | Shin et al. ............... 623/1.13 |

* cited by examiner

*Primary Examiner* — S. Thomas Hughes
*Assistant Examiner* — Jocelin Tanner
(74) *Attorney, Agent, or Firm* — IP & T Group LLP

(57) ABSTRACT

A self-expandable shape memory alloy stent includes first and second wires made of super-elastic shape memory alloy. The first wire extends downwardly from the top to the bottom of the stent without interlocking with itself but extends upwardly from the bottom to the top of the stent while interlocking with itself to leave a multiplicity of rhombic spaces. Similarly, the second wire extends downwardly from the top to the bottom of the stent without interlocking with itself but extends upwardly from the bottom to the top of the stent while interlocking with itself, in such a manner as to divide the rhombic spaces formed by the first wire into four small rhombic spaces. The first wire and the second wire are woven with each other in such a manner that the second wire passes alternately below and above the first wire at intersection points.

4 Claims, 16 Drawing Sheets

SELF-EXPANDABLE SHAPE MEMORY ALLOY STENT AND METHOD FOR FABRICATING THE SAME

BACKGROUND OF THE INVENTION

1. Field of the Invention

The present invention pertains to a self-extendable shape memory alloy stent situated in a stenosal portion of tubular organs of a living body for expanding the passage of the stenosal portion and a method for fabricating the same. More specifically, the present invention is directed to a self-extendable shape memory alloy stent and a method for fabricating the same, wherein the self-extendable stent is capable of being situated to fit the shape of the passage of the stenosal portion regardless of the passage shape, whether straight (horizontal or vertical) or curved, and is prevented from any longitudinal compression or extension and any resultant length variation when the self-extendable stent is situated in the passage of the stenosal portion by use of a guide tube, while maximizing the circumferential elasticity of the self-extendable stent, thereby allowing the tasks of placing the self-extendable stent in position and expanding the stenosal portion to be performed in an efficient manner.

2. Description of the Related Art

In general, blood vessels is often blocked or constricted due to thrombus, arteriosclerosis or the like, in which event a variety of disorders may occur. In case of the blood vessels being subjected to a stenosis, it is the recent trend that the stenosis is treated through the use of a stent without resort to a surgical operation.

Conventionally, varying kinds of stents have been developed and used. Examples of the conventional stents include a self-extendable stent that has a hollow cylindrical body comprised of a super-elastic shape memory alloy wire intersectedly woven to leave a multiplicity of rhombic spaces, the opposite ends of the wire joined to each other by welding. Unless forcibly pressed by an external force, the stent normally tends to be returned back to an original shape under the action of diametrically and longitudinally exerting elastic forces.

This type of self-extendable stent is situated in a stenosal portion by heavily reducing the volume of the cylindrical body with attendant reduction of the rhombic spaces, inserting the stent up to a target stenosal portion by use of an auxiliary instrument such as a guide tube, and pushing the stent with a pusher catheter into contact with the stenosal portion, thus allowing the stent to expand the blood vessels or like tubular organs. In this regard, the stent is designed to have a diameter 10-30% greater than that of the blood vessels and a length greater than the stenosal portion of the blood vessels.

Although the self-extendable stent noted above has no difficulty in applying it to a straight or gently curved blood vessel, it is not suitable for use in a heavily winding blood vessel. In other words, the blood vessel to which the stent is applied has a tendency to be straightened by the diametrically outwardly acting elastic force of the stent without maintaining the original winding condition. This increases the length of the blood vessel and makes the passage of the blood vessel at the opposite ends of the stent become smaller than in the pre-treatment condition, contrary to the original intent.

To avoid the afore-mentioned problems, Korean Patent Application Nos. 2001-18024 and 2001-18025 filed by the present applicant disclose self-extendable stents situated in a stenosal portion of tubular organs of a living body for expanding the passage of the stenosal portion. The self-extendable stents taught in these prior patent applications are capable of maintaining the shape of a passage of the blood vessel, whether straight (horizontal or vertical) or winding, and thus minimizing unwanted deformation of the stent-situated portion of the blood vessel. This makes the self-extendable stents very useful.

More specifically, Korean Patent Application No. 2001-18024 (hereinbelow, referred to as a "first reference") discloses a self-extendable stent of the type wherein two super-elastic shape memory alloy wires are woven in a plain weave pattern to have hooking portions and merely-intersecting portions with variable rhombic spaces left therebetween. The merely-intersecting portions are positioned between the hooking portions. The hooking portions allow the stent to be shrunk in a longitudinal direction, while the merely-intersecting portions serve to resist the longitudinal shrinkage of the stent. One of the wires is extended a diagonal length of l in a slanted circumferential direction and then turned to a different direction at a transition point. Such an extending and turning process is repeatedly conducted with respect to a multiplicity of transition points. The other of the wires is extended a diagonal length of $2\ell$ in a slanted circumferential direction and then turned to a different direction at a transition point. Such an extending and turning process is repeatedly conducted with respect to a multiplicity of transition points. In this regard, the "$\ell$" denotes the distance between two neighboring transition points where projecting pins are located in fabricating the stent with a jig.

On the other hand, Korean Patent Application No. 2001-18024 (hereinbelow, referred to as a "second reference") discloses a self-extendable stent of the type wherein first and second super-elastic shape memory alloy wires are used respectively to form a primary stent member and a secondary stent member, both of which are overlaid in a radial direction. The primary stent member is fabricated by weaving the first wire in a plain weave pattern to have hooking portions and merely-intersecting portions with variable rhombic spaces left therebetween. The hooking portions allow the stent to be shrunk in a longitudinal direction, while the merely-intersecting portions serve to resist the longitudinal shrinkage of the stent. Furthermore, the secondary stent member is fabricated by diagonally extending the first wire from the top to the bottom of a cylindrical jig in a parallel relationship with the first wire of the primary stent member in such a manner that the second wire can equally divide the rhombic spaces of the primary stent member into four small spaces.

According to the self-extendable stents disclosed in the first and second references, the variable rhombic spaces formed between the hooking portions and the merely-intersecting portions are capable of being deformed by an external force, while allowing the stents to maintain elasticity in a diametrical direction. Thus, even when situated in heavily winding stenosal portion, the self-extendable stents can keep the stenosal portions of the tubular organs, such as blood vessels, a gullet, a gall duct and a urethra, in their original winding shape, while expanding the passages of the stenosal portions.

The self-extendable stents of the first and second references noted above have advantages and disadvantages in their own way.

In case of the first reference, the self-extendable stent undergoes severe contraction and extension in the longitudinal direction, because two wires are woven to have hooking portions and merely-intersecting portions. In other words, the self-extendable stent of the first reference has an advantage in that it can be flexibly deformed in conformity with the shape of a target stenosal portion. However, the self-extendable stent of the first reference is easily contracted or extended in the longitudinal direction and thus undergoes severe length variation when the stent is loaded to and unloaded from a guide tube. This reduces workability in the process of situating the stent in position. Moreover, no uniform expanding force acts on the stenosal portion if the stent is situated in the stenosal portion under a longitudinally unevenly contracted condition.

In contrast, the self-extendable stent of the second reference is free from any contraction and extension in the longitudinal direction, because the first wire constituting the primary stent member is woven to have hooking portions and merely-intersecting portions but the second wire constituting the secondary stent member has a straight portion extending from the top to the bottom with no hooking or turning. However, in case of the self-extendable stent of the second reference, the straight portion of the second wire makes it difficult for the stent to be flexed in conformity with the shape of a winding stenosal portion. Furthermore, the straight portion of the second wire reduces elasticity of the stent in a circumferential direction, which makes it difficult to effectively expand the passage of the stenosal portion and then keep the passage in the expanded condition.

Accordingly, a demand has existed for a self-extendable stent that can enjoy the advantages offered by the stents of the first and second references, namely, a self-extendable stent of the type exhibiting reduced length variation, enhanced flexibility and maximized circumferential elasticity.

SUMMARY OF THE INVENTION

In view of the problems inherent in the prior art references cited above, it is an object of the present invention to provide a self-expandable stent that can expand the passage of a stenosal portion of a living body, the stent having an ability to flexibly conform to and maintain the shape of passage of the stenosal portion, whether straight (horizontal or vertical) or winding, thus minimizing unwanted deformation of the stenosal portions, the stent also designed to be easily installed in and effectively expand the stenosal portion by preventing any inadvertent length variation, such as longitudinal contraction and extension, in the process of installing the same with the use of a guide tube, while maximizing its elasticity in a circumferential direction.

According to one aspect of the present invention, there is provided a method for fabricating a self-expandable shape memory alloy stent, comprising the steps of:

providing a base jig including a cylinder and a plurality of radially outwardly projecting pins, the cylinder having a plurality of circumference dividing lines (a0, a1, a2, a3 . . . and a19) and a plurality of length dividing lines (b0, b1, b2, b3 . . . and b26) defined by equally dividing a circumference W and a length L of the cylinder, the circumference dividing lines intersecting the length dividing lines to form a plurality of wire transition points at their intersections, the projecting pins implanted to the cylinder at the transition points;

fabricating a primary stent member by extending a first shape memory alloy wire downwardly from a first top starting point to a projecting pin of a first primary transition point disposed at an uppermost position of the cylinder, then diagonally downwardly from the projecting pin of the first primary transition point to a projecting pin of a second primary transition point by a first diagonal length, then diagonally upwardly from the projecting pin of the second primary transition point to a projecting pin of a third primary transition point by a second diagonal length one half time smaller than the first diagonal length, then diagonally downwardly from the projecting pin of the third primary transition point to a projecting pin of a fourth primary transition point by a third diagonal length multiple times greater than the second diagonal length, then diagonally upwardly from the projecting pin of the fourth primary transition point to a projecting pin of a fifth primary transition point by the second diagonal length, and then diagonally downwardly by the first diagonal length from the projecting pin of the fifth primary transition point to a projecting pin of a sixth primary transition point disposed at a lowermost position of the cylinder, extending the first wire in zigzag from the projecting pin of the sixth primary transition point along a circumferential direction of the cylinder to form a lowermost cylindrical zigzag part, extending the first wire upwardly from the lowermost zigzag part in such a manner as to form a plurality of middle cylindrical zigzag parts and an uppermost cylindrical zigzag part, the lowermost, middle and uppermost zigzag parts being interlocked with one another to leave a plurality of rhombic spaces therebetween; and fabricating a secondary stent member by extending a second shape memory alloy wire downwardly from a second top starting point to a projecting pin of a first secondary transition point disposed at an uppermost position of the cylinder, then diagonally downwardly from the projecting pin of the first secondary transition point to a projecting pin of a second secondary transition point by a first diagonal length, then diagonally upwardly from the projecting pin of the second secondary transition point to a projecting pin of a third secondary transition point by a second diagonal length one half time smaller than the first diagonal length, then diagonally downwardly from the projecting pin of the third secondary transition point to a projecting pin of a fourth secondary transition point by a third diagonal length multiple times greater than the second diagonal length, then diagonally upwardly from the projecting pin of the fourth secondary transition point to a projecting pin of a fifth secondary transition point by the second diagonal length, and then diagonally downwardly by the first diagonal length from the projecting pin of the fifth secondary transition point to a projecting pin of a sixth secondary transition point disposed at a lowermost position of the cylinder, extending the second wire in zigzag from the projecting pin of the sixth secondary transition point along a circumferential direction of the cylinder to form a lowermost cylindrical zigzag part, extending the second wire upwardly from the lowermost zigzag part in such a manner as to form a plurality of middle cylindrical zigzag parts and an uppermost cylindrical zigzag part, the lowermost, middle and uppermost zigzag parts of the second wire being interlocked with one another to leave a plurality of rhombic spaces therebetween, wherein the second wire of the secondary stent member is arranged to intersect the first wire of the primary stent member at a multiplicity of intersection points and wherein the first wire and the second wire are woven with each other in such a manner that the second wire passes alternately below and above the first wire at the intersection points According to another aspect of the present invention, there is provided a self-expandable shape memory alloy stent comprising:

a first wire made of super-elastic shape memory alloy, the first wire extending downwardly from a first top starting point to a first primary transition point disposed at an uppermost position of the stent, diagonally downwardly extending from the first primary transition point to a second primary transition point by a first diagonal length, diagonally upwardly extending from the second primary transition point to a third primary transition point by a second diagonal length one half time smaller than the first diagonal length, diagonally downwardly extending from the third primary transition point to a fourth primary transition point by a third diagonal length multiple times greater than the second diagonal length, diagonally upwardly extending from the fourth primary transition point to a fifth primary transition point by the second diagonal length, and then diagonally downwardly extending by the first diagonal length from the fifth primary transition point to a sixth primary transition point disposed at a lowermost position of the stent, the first wire extending in zigzag from the sixth primary transition point along a circumferential direction of the stent to form a lowermost cylindrical zigzag part, the first wire extending upwardly from the lowermost zigzag part in such a manner as to form a plurality of middle cylindrical zigzag parts and an uppermost cylindrical zigzag part, the lowermost, middle and uppermost zigzag parts being interlocked with one another to leave a plurality of rhombic spaces therebetween; and a second wire made of super-elastic shape memory alloy, the second wire extending downwardly from a second top starting point to a first secondary transition point disposed at an uppermost position of the stent, diagonally downwardly extending from the first secondary transition point to a second secondary transition point by a first diagonal length, diagonally upwardly extending from the second secondary transition point to a third secondary transition point by a second diagonal length one half time smaller than the first diagonal length, diagonally downwardly extending from the third secondary transition point to a fourth secondary transition point by a third diagonal length multiple times greater than the second diagonal length, diagonally upwardly extending from the fourth secondary transition point to a fifth secondary transition point by the second diagonal length, and then diagonally downwardly extending by the first diagonal length from the fifth secondary transition point to a sixth secondary transition point disposed at a lowermost position of the stent, the second wire extending in zigzag from the sixth secondary transition point along a circumferential direction of the stent to form a lowermost cylindrical zigzag part, the second wire extending upwardly from the lowermost zigzag part in such a manner as to form a plurality of middle cylindrical zigzag parts and an uppermost cylindrical zigzag part, the lowermost, middle and uppermost zigzag parts of the second wire being interlocked with one another to leave a plurality of rhombic spaces therebetween, wherein the second wire is arranged to intersect the first wire at a multiplicity of intersection points and wherein the first wire and the second wire are woven with each other in such a manner that the second wire passes alternately below and above the first wire at the intersection points.

BRIEF DESCRIPTION OF THE DRAWINGS

The above and other objects, features and advantages of the present invention will become apparent from the following description of preferred embodiments given in conjunction with the accompanying drawings, in which:

FIGS. 6a and 6b are partially enlarged views showing certain portions of the stent illustrated in FIG. 5, wherein FIG. 6a shows the stent in a normal expanded condition but FIG. 6a illustrates the stent in a diametrically contracted condition;

DETAILED DESCRIPTION OF THE INVENTION

Figure 1:
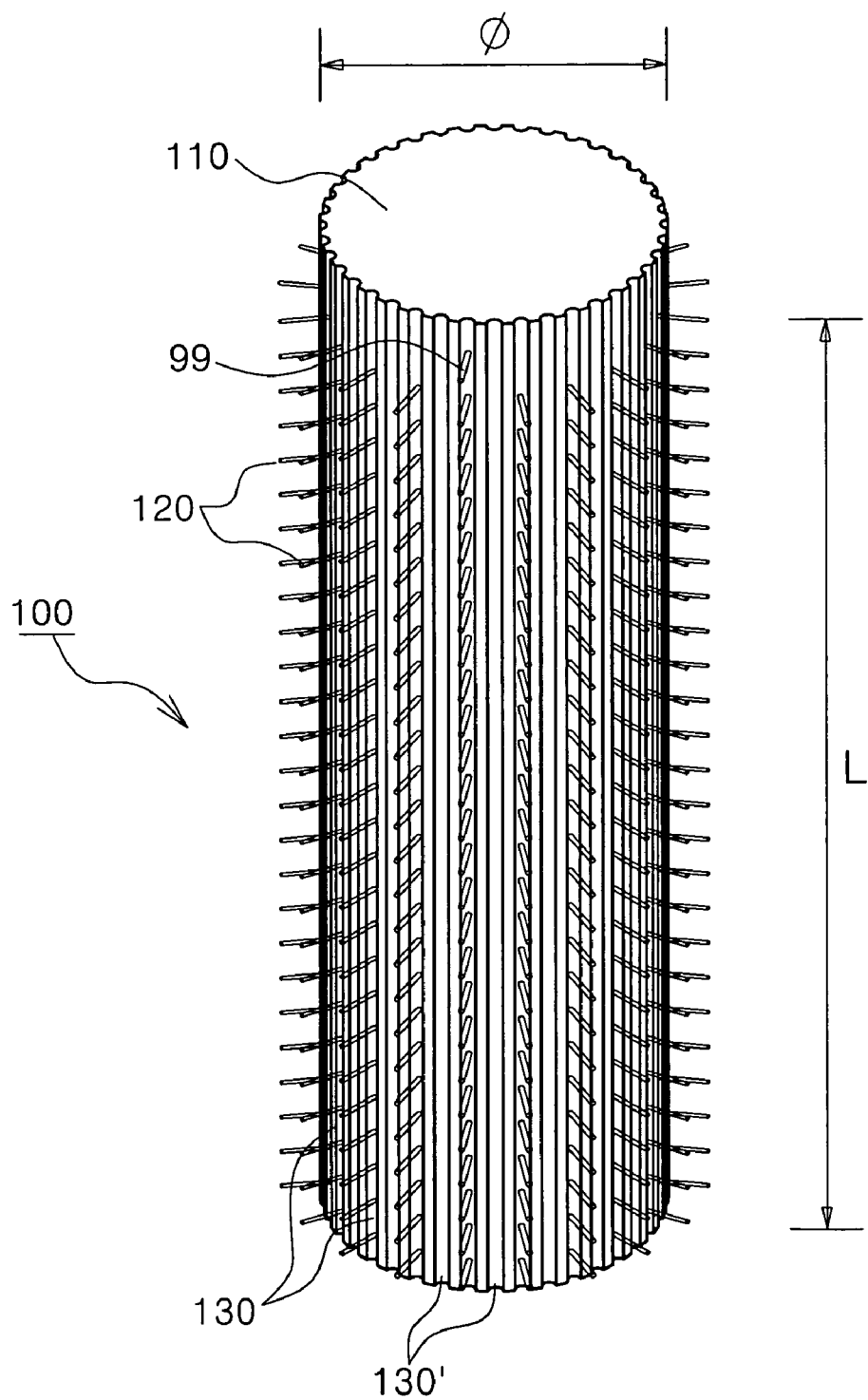
FIG. 1 is a perspective view showing a base jig used for the purpose of embodying the present invention.

Hereinbelow, one preferred embodiment of the present invention will be described in detail with reference to the accompanying drawings.

The material of a wire employed in the present invention is a shape memory alloy which is the same as that of the invention of patent applications previously filed in Korea by the inventors of the present application. One of the most preferred wire materials is a nickel-titanium (Ni—Ti)-based alloy.

The self-expandable stent 80 of the present invention is fabricated using first and second super-elastic shape memory alloy wires 10 and 11 each having a diameter in the range of 0.1 to 0.5 mm. The first wire 10 and the second wire 11 constitute a primary stent member X and a secondary stent member Y woven with each other to provide the self-extendable stent 80.

Assuming that the stent 80 is placed upright and viewed from the front side, the first wire 10 extends downwardly from the top to the bottom of the stent 80 without interlocking with itself but extends upwardly from the bottom to the top of the stent 80 while interlocking with itself to leave a multiplicity of rhombic spaces. Similarly, the second wire 11 extends downwardly from the top to the bottom of the stent 80 without interlocking with itself but extends upwardly from the bottom to the top of the stent 80 while interlocking with itself, in such a manner as to divide the rhombic spaces formed by the first wire 10 into four small rhombic spaces. The first wire 10 and the second wire are 11 woven with each other in such a manner that the second wire 11 passes alternately below and above the first wire 10 at intersection points. These features will become apparent from the following description.

Figure 2:
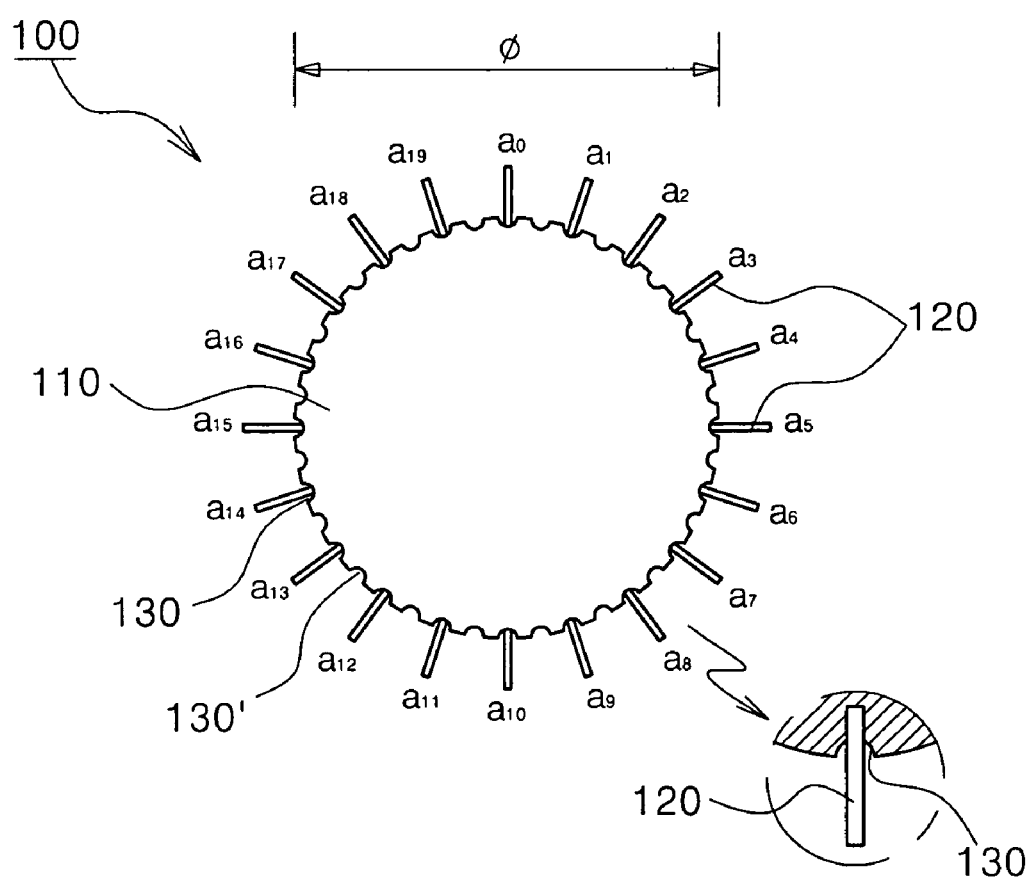
FIG. 2 is a top view of the base jig shown in FIG. 1, with a portion thereof illustrated in a microscopically exaggerated condition.

According to the present invention, a base jig 100 shown in FIGS. 1 and 2 is used to fabricate the self-expandable stent 80. The base jig includes a cylinder 110 having a diameter ø, a circumference W and a length L. A plurality of circumference dividing lines a0, a1, a2, a3 . . . and a19 and a plurality of length dividing lines b0, b1, b2, b3 . . . and b26 are set by equally dividing the circumference W and the length L, respectively.

A plurality of weaving grooves 130 are formed along the circumference dividing lines a0, a1, a2, a3 . . . and a19 in a longitudinal direction of the cylinder 110. A plurality of projecting pins 120 are detachably implanted at all the intersection points, i.e., transition points, between the circumference dividing lines a0, a1, a2, a3 . . . and a19 and the length dividing lines b0, b1, b2, b3 . . . and b26. A plurality of auxiliary weaving grooves 130' are respectively formed between two neighboring weaving grooves 130, thus constructing the base jig 100. An anchor pin 99 or 99' is implanted at the uppermost position of the base jig 100 in a diametrically opposing relationship with each other.

It should be appreciated that the above-noted setting is merely for the understanding of the present invention. In other words, although the present invention is described using the circumference dividing lines a0, a1, a2, a3 ... and a19 and the length dividing lines b0, b1, b2, b3 ... and b26 set by equally dividing the circumference W and the length L of the cylinder 110 of the base jig 100, this is merely to assure easier understanding of the present invention. Accordingly, the circumference dividing lines and the length dividing lines may be greater or lesser in number depending on the size of the self-expandable stent 80, i.e., the diameter and length thereof.

Description will be given to a process for fabricating the self-expandable stent 80 of the present invention through the use of the above-mentioned base jig 100, with reference to FIGS. 3 and 4 which illustrate the base jig 100 in a developed condition to explain the stent fabricating process.

Figure 3A:
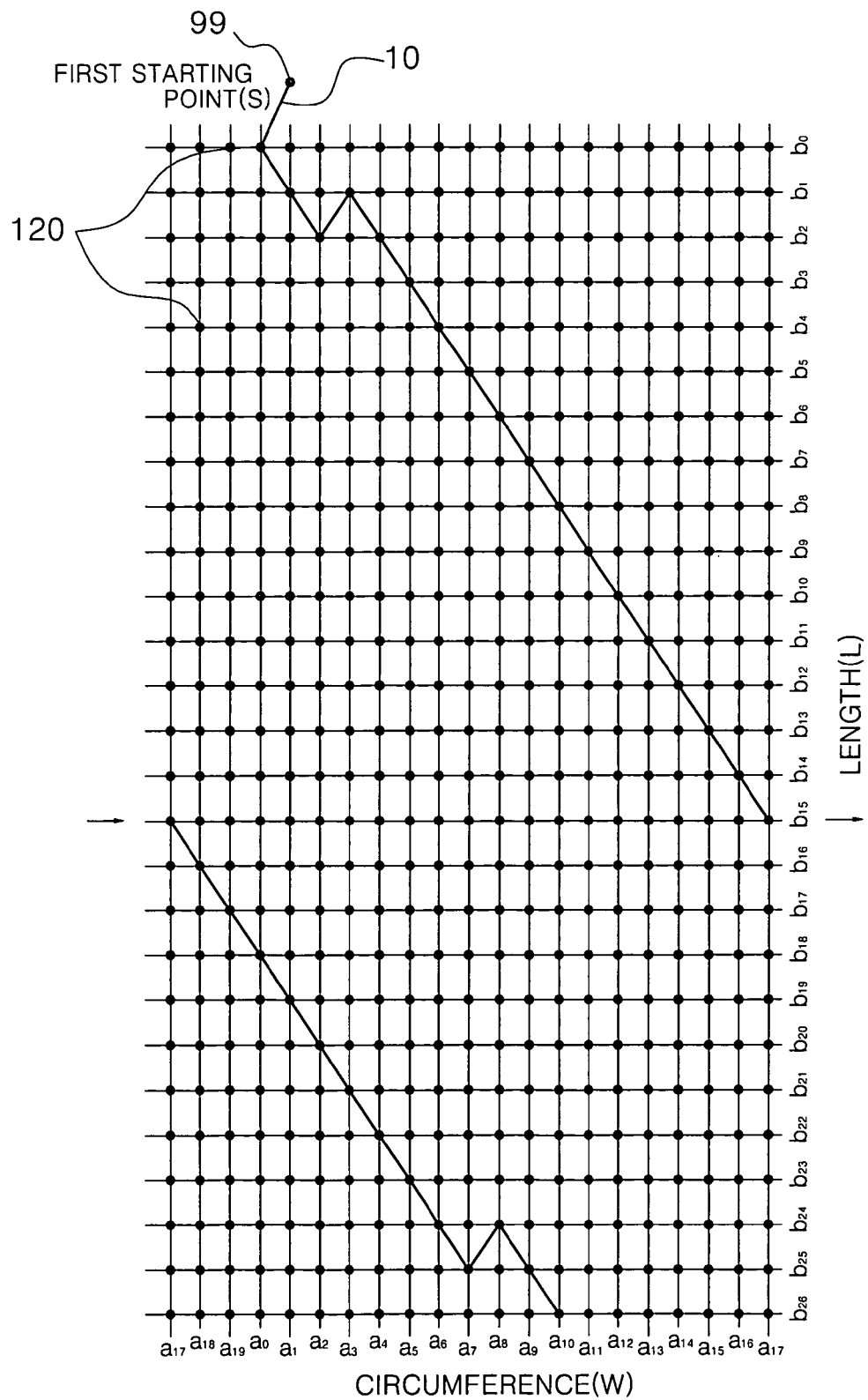
FIGS. 3a through 3e are development views illustrating a process of producing a first stent member.

Referring first to FIG. 3a, in order to fabricate the primary stent member X, a knot is formed by tying the proximal end of the first wire 10 and insertedly secured to the anchor pin 99. The knot serves as a first top starting point S from which the first wire 10 begins to extend downwardly toward a multiplicity of transition points. Through the specification, the term "transition points" mean the intersecting points between the circumference dividing lines a0, a1, a2, a3 ... and a19 and the length dividing lines b0, b1, b2, b3 ... and b26 of the base jig 100.

The first wire 10 is extended downwardly from the first top starting point S to a projecting pin of a first primary transition point a0b0 disposed at an uppermost circumference dividing line b0 of the cylinder 110 of the base jig 100.

Turning the left side of the projecting pin of the first primary transition point a0b0, the first wire 10 is then extended diagonally downwardly to a projecting pin of a second primary transition point a2b2 by a first diagonal length $2\ell$, where the $\ell$ denotes the distance between two diagonally neighboring transition points.

Turning the lower side of the projecting pin of the second primary transition point a2b2, the first wire 10 is then extended diagonally upwardly to a projecting pin of a third primary transition point a3b1 by a second diagonal length $\ell$ which is one half time smaller than the first diagonal length $2\ell$.

Turning the upper side of the projecting pin of the third primary transition point a3b1, the first wire 10 is then extended long diagonally downwardly to a projecting pin of a fourth primary transition point a7b25 by a third diagonal length which is multiple times, e.g., 24 times, greater than the second diagonal length $\ell$.

Turning the lower side of the projecting pin of the fourth primary transition point a7b25, the first wire 10 is then extended diagonally upwardly to a projecting pin of a fifth primary transition point a8b24 by the second diagonal length $\ell$.

Turning the upper side of the projecting pin of the fifth primary transition point a8b24, the first wire 10 is then extended diagonally downwardly by the first diagonal length $2\ell$ to a projecting pin of a sixth primary transition point a10b26 disposed at a lowermost circumference dividing line b26 of the cylinder 110 of the base jig 100.

This creates a downward extension part 75 (see FIG. 6a) which extends between the first primary transition point a0b0 disposed at the uppermost circumference dividing line b0 of the cylinder 110 of the base jig 100 and the sixth primary transition point a10b26 disposed at a lowermost circumference dividing line b26 of the cylinder 110 of the base jig 100. The downward extension part 75 of the first wire 10 serves to restrain the longitudinal contraction or extension, i.e., the length variation of the stent 80.

Figure 3B:
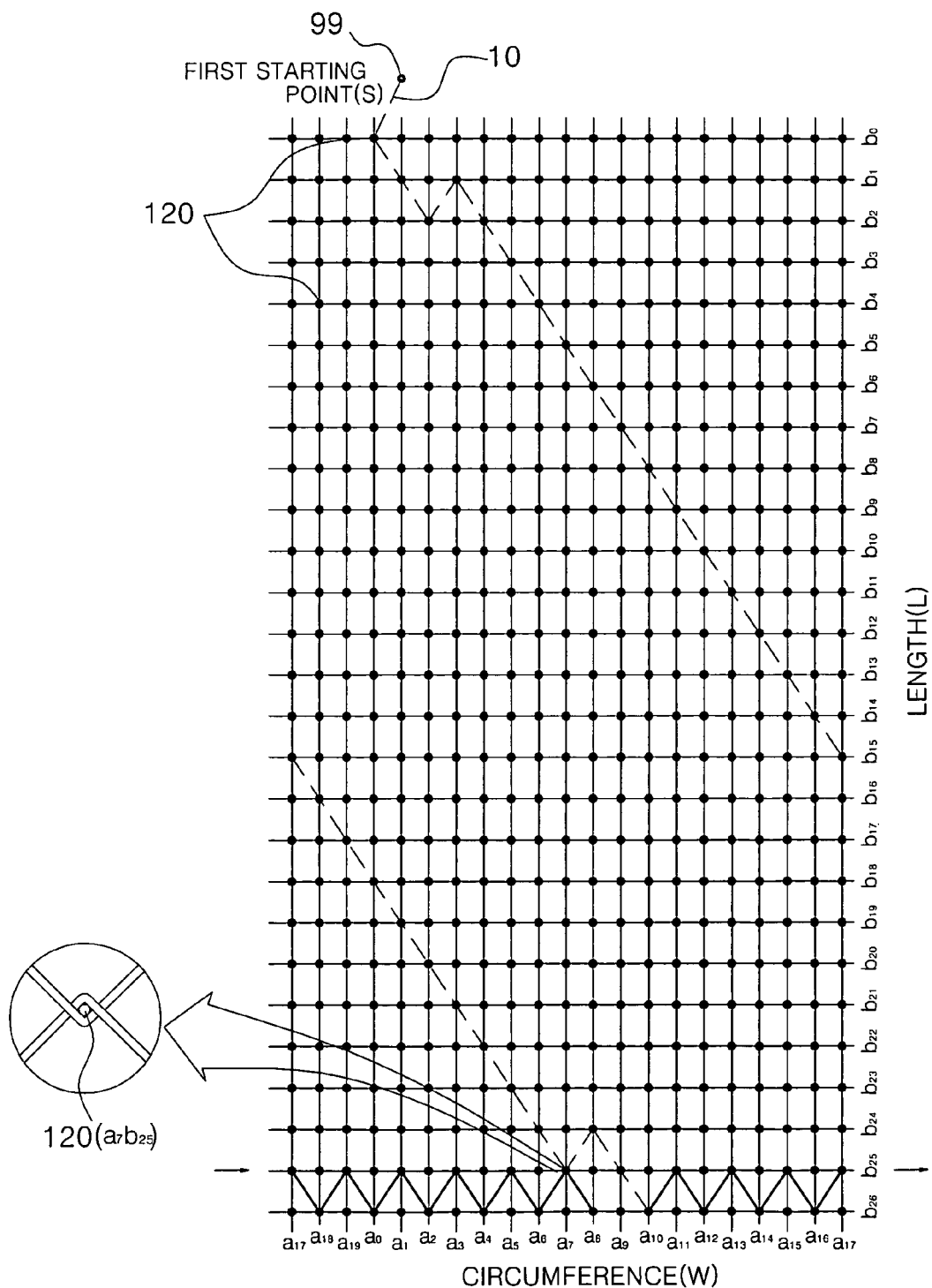

Referring to FIG. 3b, the first wire 10 is then extended in zigzag from the projecting pin of the sixth primary transition point a10b26 along a circumferential direction of the cylinder 110 to form a lowermost cylindrical zigzag part shown in thick solid lines, at which time the first wire 10 turns around a plurality of projecting pins disposed at the circumference dividing lines a10 through a8 along the length dividing lines b25 and b26. The lowermost cylindrical zigzag part is interlocked with the part of the first wire 10 at the fourth transition point a7b25, as microscopically illustrated in FIG. 3b.

Figure 3C:
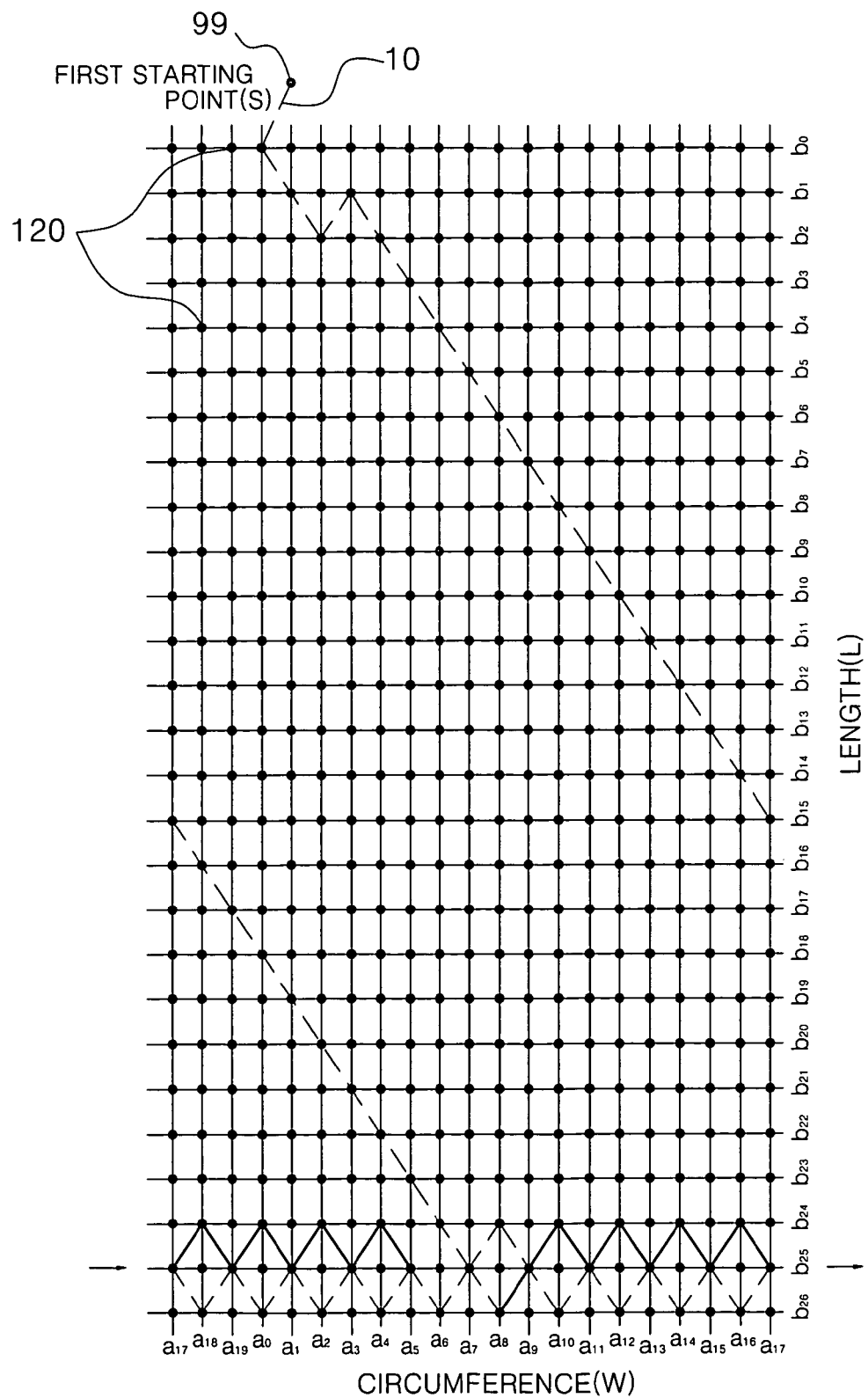
Figure 3D:
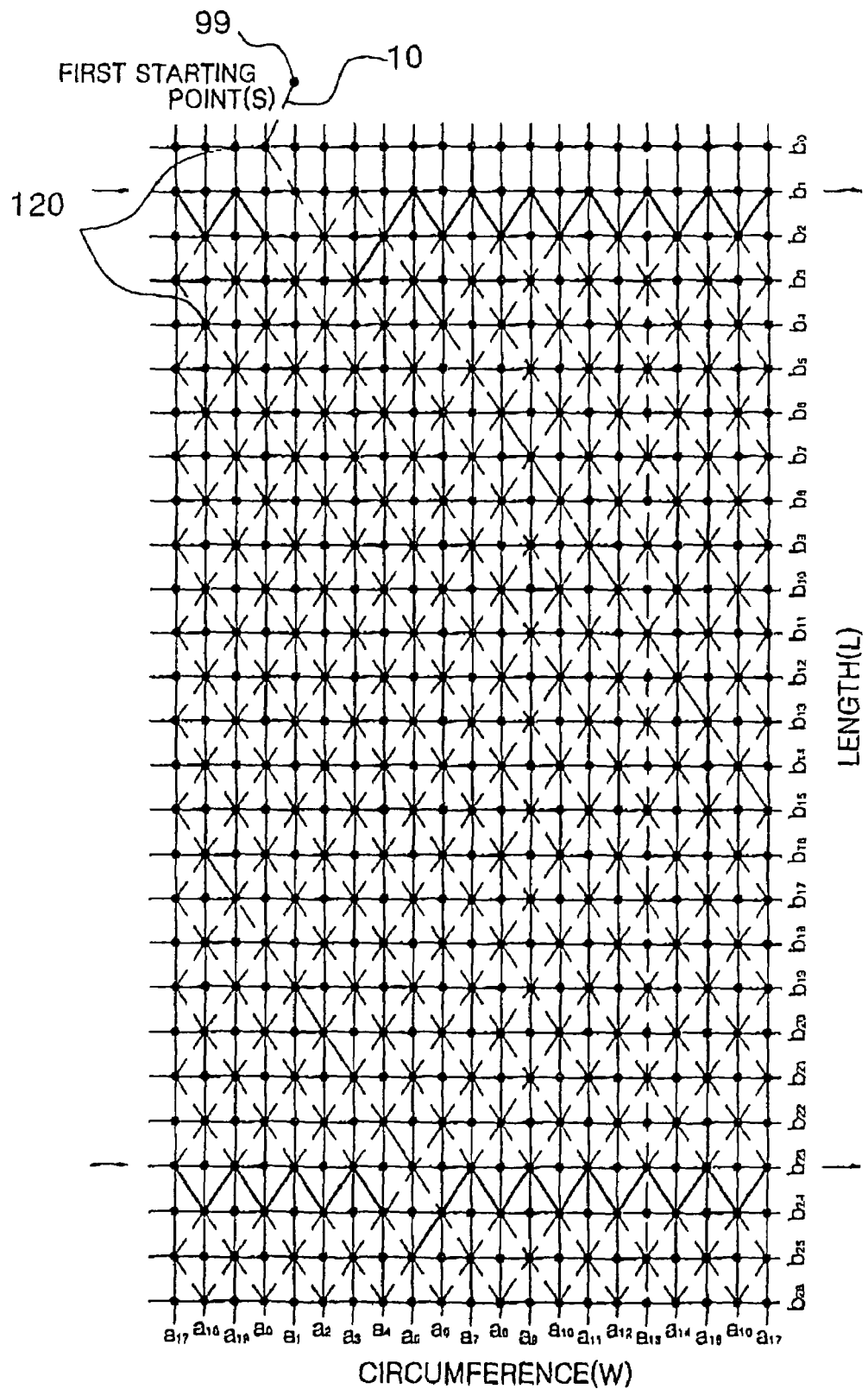

Turning to FIGS. 3c and 3d, the first wire 10 is extended upwardly from the lowermost zigzag part and then runs in zigzag along a circumferential direction of the cylinder 110 in such a manner as to form a plurality of middle cylindrical zigzag parts lying one above another in between the length dividing lines b25 through b1, as depicted in thick solid lines and thin dotted lines. The middle zigzag parts are interlocked with the part of the first wire 10 at the fifth primary transition point a8b24 and also at the second primary transition point a2b2. The number of the middle cylindrical zigzag parts is not subjected to any restriction and therefore may be changed depending on the length of the self-extendable stent 80 to be fabricated.

Figure 3E:
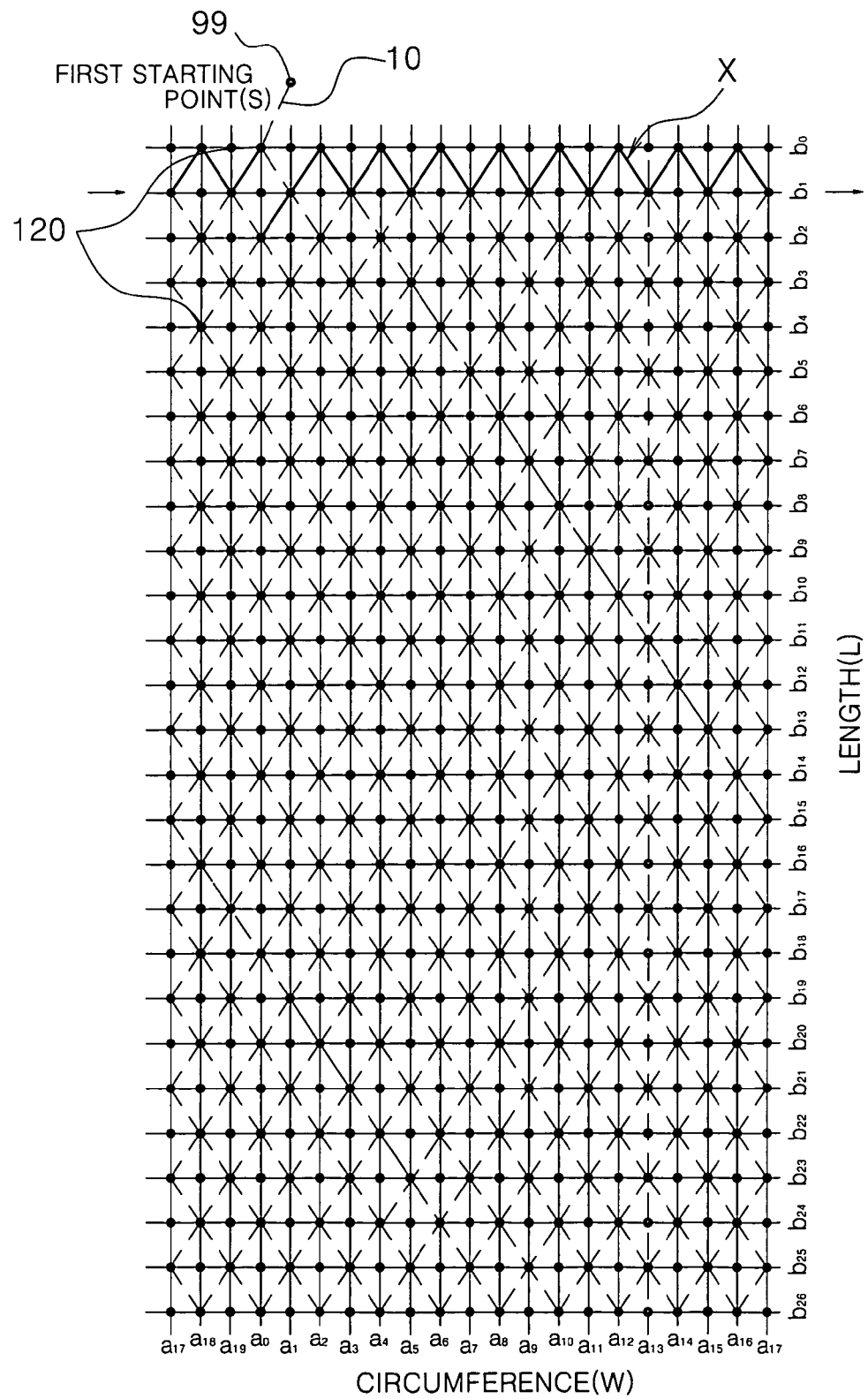
Figure 5:
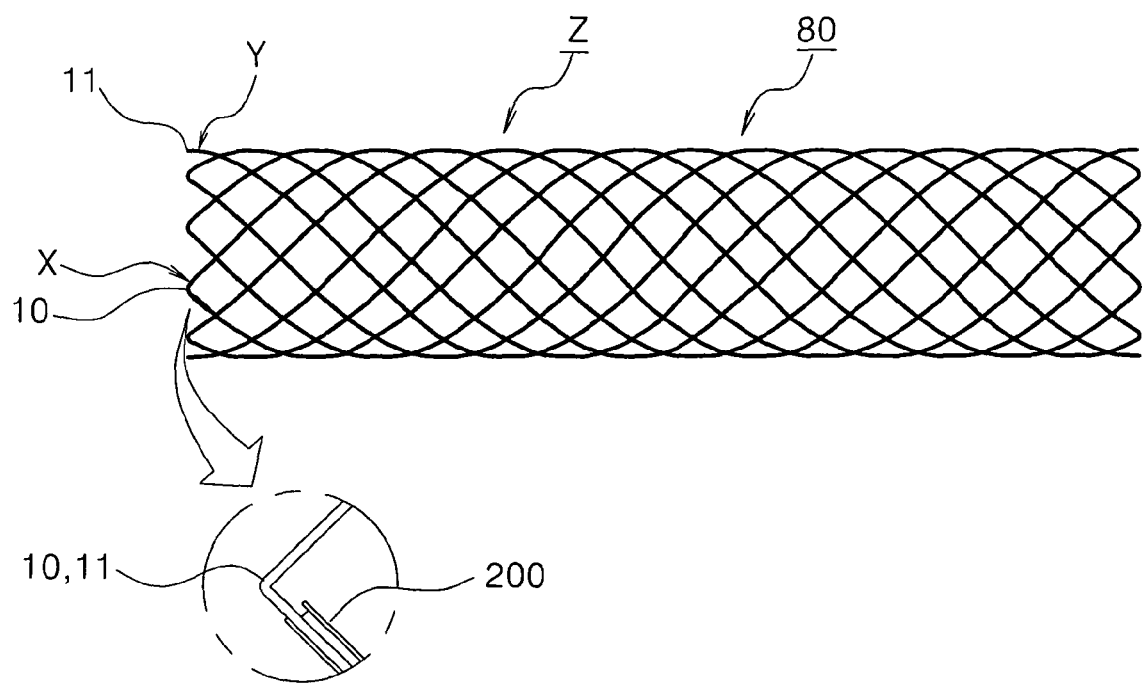
FIG. 5 is a schematic front view showing a self-expandable stent in accordance with the present invention.

Referring to FIG. 3e, the first wire 10 is extended upwardly from the uppermost one of the middle zigzag parts and then runs in zigzag along a circumferential direction of the cylinder 110 in such a manner as to form an uppermost cylindrical zigzag part as depicted in thick solid lines. The uppermost cylindrical zigzag part is interlocked with the part of the first wire 10 at the third primary transition point a3b1. The distal end of the first wire 10 is bonded to itself at the first primary transition point a0b0 in the vicinity of the first top starting point S. The bonding task is conducted by means of, e.g., a collapsible sleeve 200, as illustrated in FIG. 5 or by welding.

In this regard, the lowermost, middle and uppermost zigzag parts of the first wire 10 are joined to one another by primary connecting wire parts each extending the first diagonal length $2\ell$ between the adjoining zigzag parts in a diagonally upward direction.

Figure 6A:
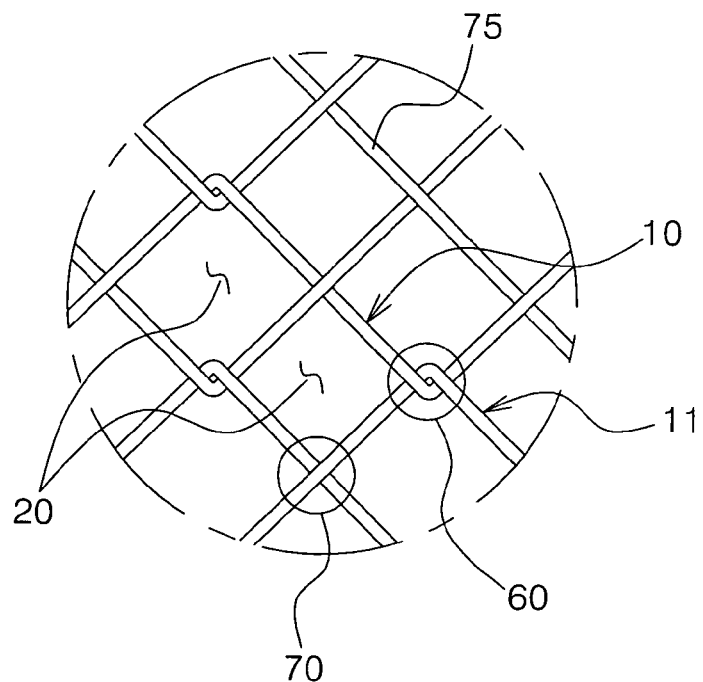

As illustrated in FIG. 6a, the lowermost, middle and uppermost zigzag parts of the first wire 10 are interlocked with one another at interlocking portions 60 to leave a plurality of rhombic spaces 20 therebetween, thereby completing the primary stent member X of the self-extendable stent 80. The weaving grooves 130 provide wire moving passages, thus making it easier to conduct the task of interlocking the zigzag parts of the first wire 10.

Figure 6B:
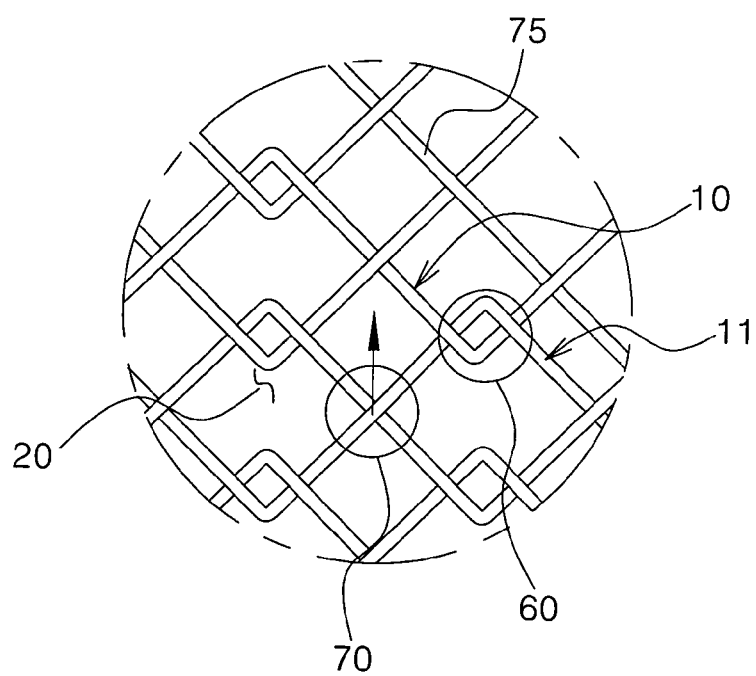

It should be appreciated that the first wire 10 is not interlocked with itself at the downward extension part 75 that runs from the top to the bottom of the self-extendable stent 80 but interlocked with itself when it extends upwardly through the lowermost, middle and uppermost zigzag parts. The primary stent member X thus fabricated can be diametrically contracted within a predetermined extent, as shown in FIG. 6b, but undue longitudinal contraction or extension of the primary stent member X is prevented due to the presence of the downward extension part 75.

Every other projecting pin 120 is used in the process of fabricating the primary stent member X with the first wire 10, with the remaining projecting pins 120 left for the fabrication of the secondary stent member Y described below.

Figure 4A:
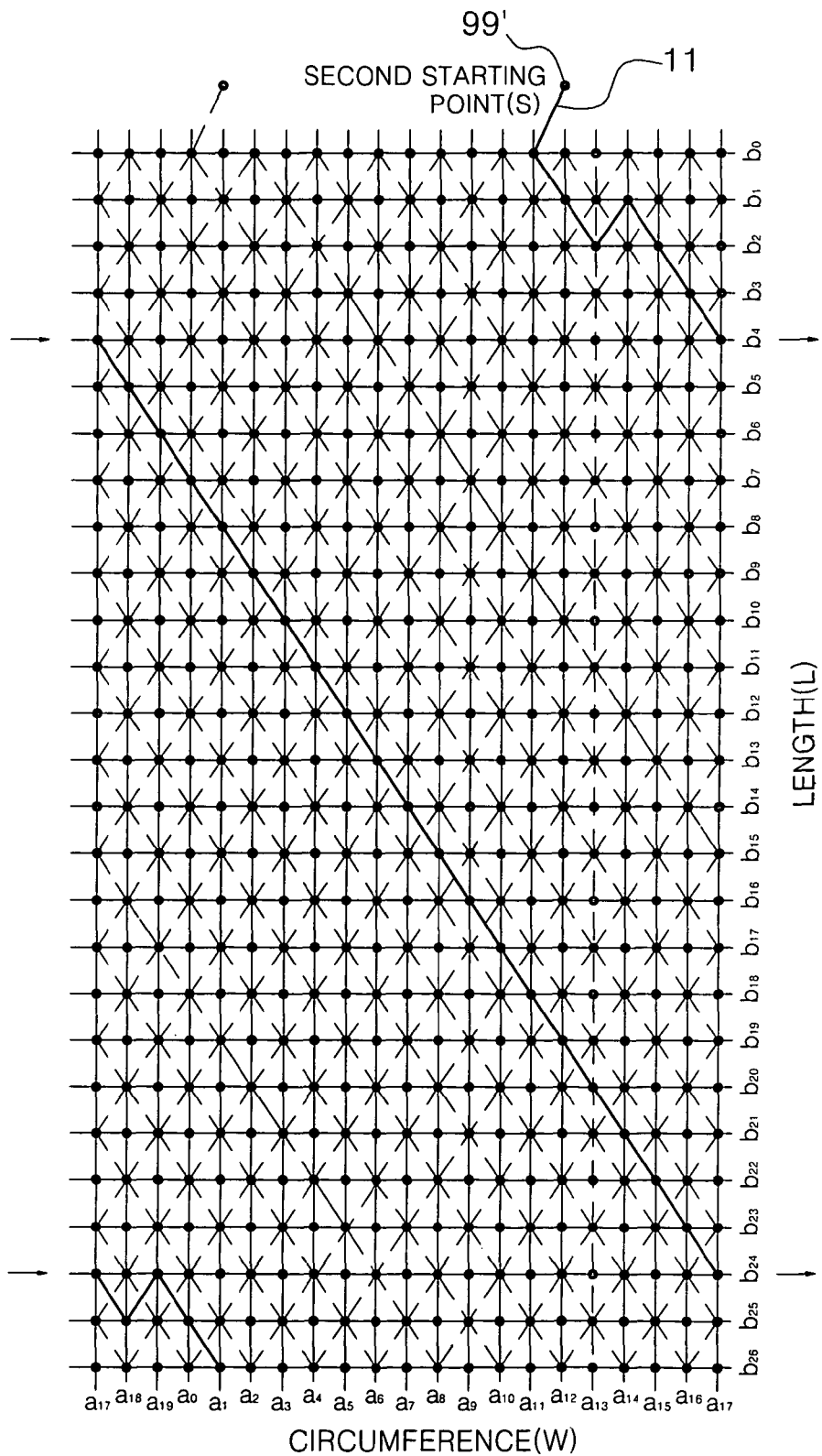
FIGS. 4a through 4e are development views illustrating a process of forming a second stent member woven with the first stent member.

Referring to FIG. 4a, in order to fabricate the secondary stent member Y, a knot is formed by tying the proximal end of the second wire 11 and insertedly secured to the anchor pin 99' lying diametrically opposite from the anchor pin 99. The knot serves as a second top starting point S from which the second wire 11 begins to extend downwardly toward a multiplicity of transition points.

As shown in thick solid lines in FIG. 4a, the second wire 11 is extended downwardly from the second top starting point S to a projecting pin of a first secondary transition point a11b0 disposed at an uppermost circumference dividing line b0 of the cylinder 110 of the base jig 100.

Turning the left side of the projecting pin of the first secondary transition point a11b0, the second wire 11 is then extended diagonally downwardly to a projecting pin of a second secondary transition point a13b2 by a first diagonal length 2ℓ, where the ℓ denotes the distance between two diagonally neighboring transition points.

Turning the lower side of the projecting pin of the second secondary transition point a13b2, the second wire 11 is then extended diagonally upwardly to a projecting pin of a third secondary transition point a14b1 by a second diagonal length ℓ which is one half time smaller than the first diagonal length 2ℓ.

Turning the upper side of the projecting pin of the third secondary transition point a14b1, the second wire 11 is then extended long diagonally downwardly to a projecting pin of a fourth secondary transition point a18b25 by a third diagonal length which is multiple times, e.g., 24 times, greater than the second diagonal length ℓ.

Turning the lower side of the projecting pin of the fourth secondary transition point a18b25, the second wire 11 is then extended diagonally upwardly to a projecting pin of a fifth secondary transition point a19b24 by the second diagonal length ℓ.

Turning the upper side of the projecting pin of the fifth secondary transition point a19b24, the second wire 11 is then extended diagonally downwardly by the first diagonal length 2ℓ to a projecting pin of a sixth secondary transition point a1b26 disposed at a lowermost circumference dividing line b26 of the cylinder 110 of the base jig 100.

This creates a downward extension part 75 (see FIG. 6a) which extends between the first secondary transition point a11b0 disposed at the uppermost circumference dividing line b0 of the cylinder 110 of the base jig 100 and the sixth secondary transition point a1b26 disposed at a lowermost circumference dividing line b26 of the cylinder 110 of the base jig 100. The downward extension part 75 of the second wire 11 serves to restrain the longitudinal contraction or extension, i.e., the length variation of the stent 80.

Figure 4B:
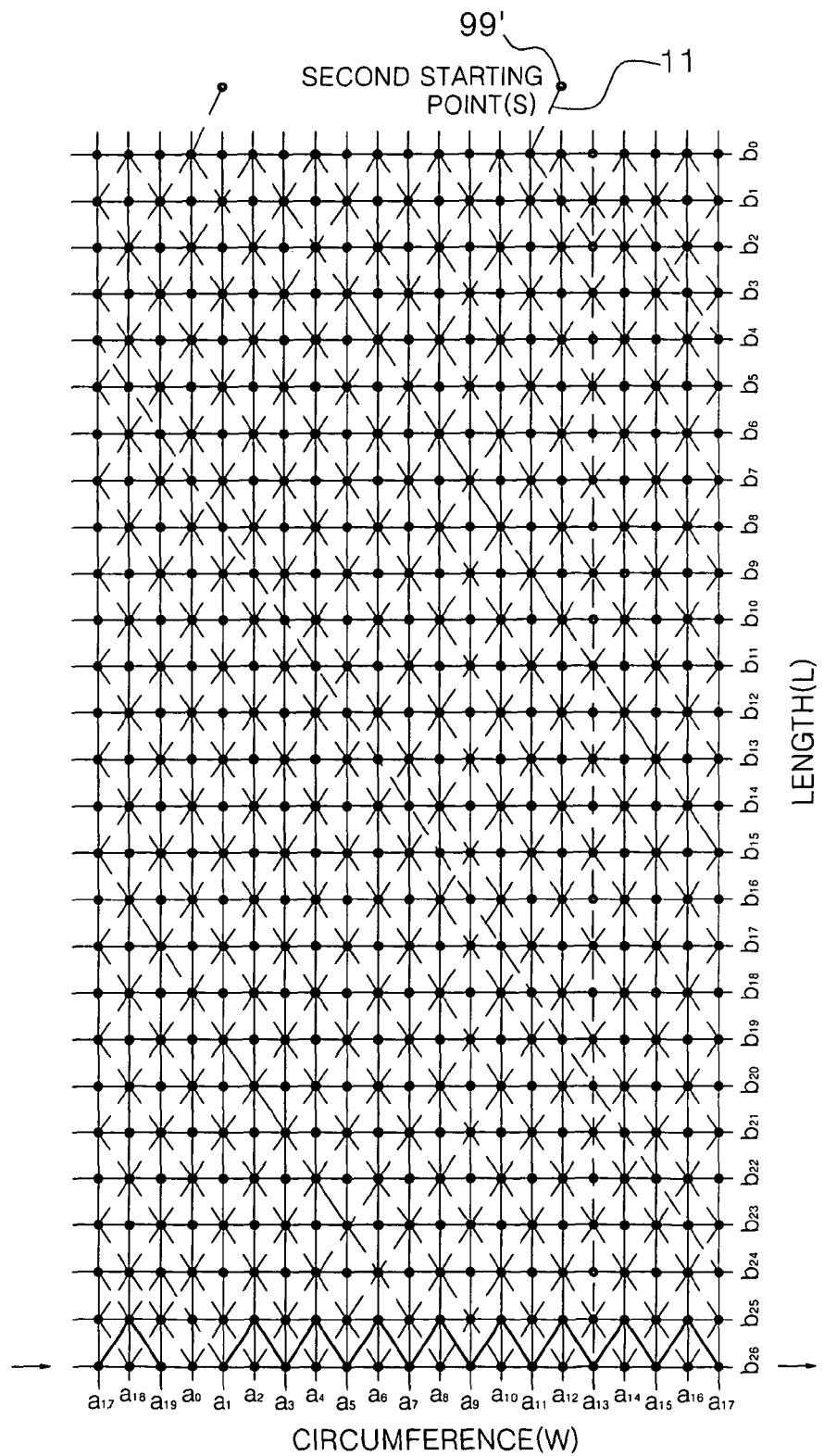

Referring to FIG. 4b, the second wire 11 is then extended in zigzag from the projecting pin of the sixth secondary transition point a1b26 along a circumferential direction of the cylinder 110 to form a lowermost cylindrical zigzag part shown in thick solid lines, at which time the second wire 11 turns around a plurality of projecting pins disposed at the circumference dividing lines a1 through a19 along the length dividing lines b25 and b26. The lowermost cylindrical zigzag part is interlocked with the part of the second wire 11 at the fourth transition point a18b25.

Figure 4C:
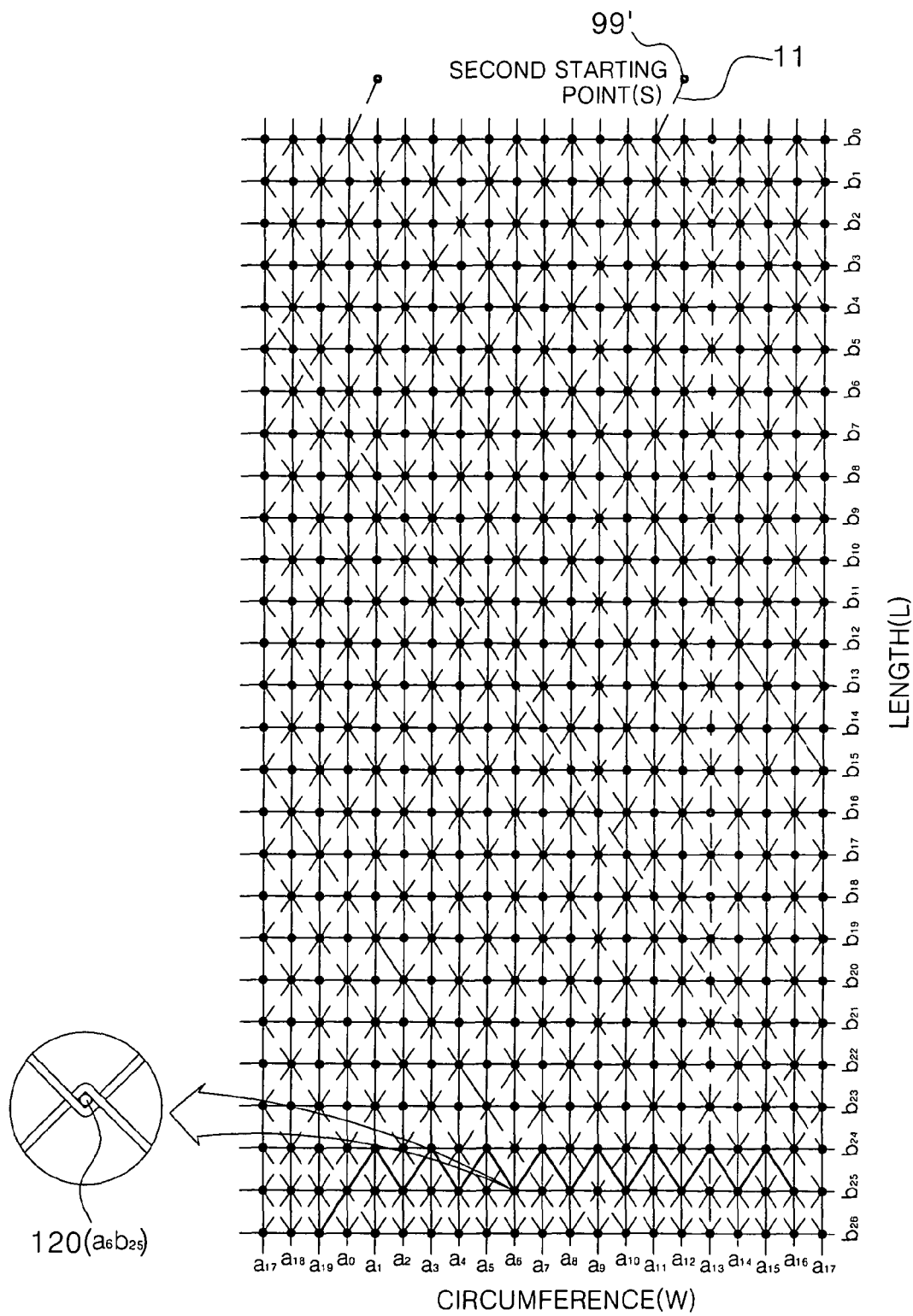
Figure 4D:
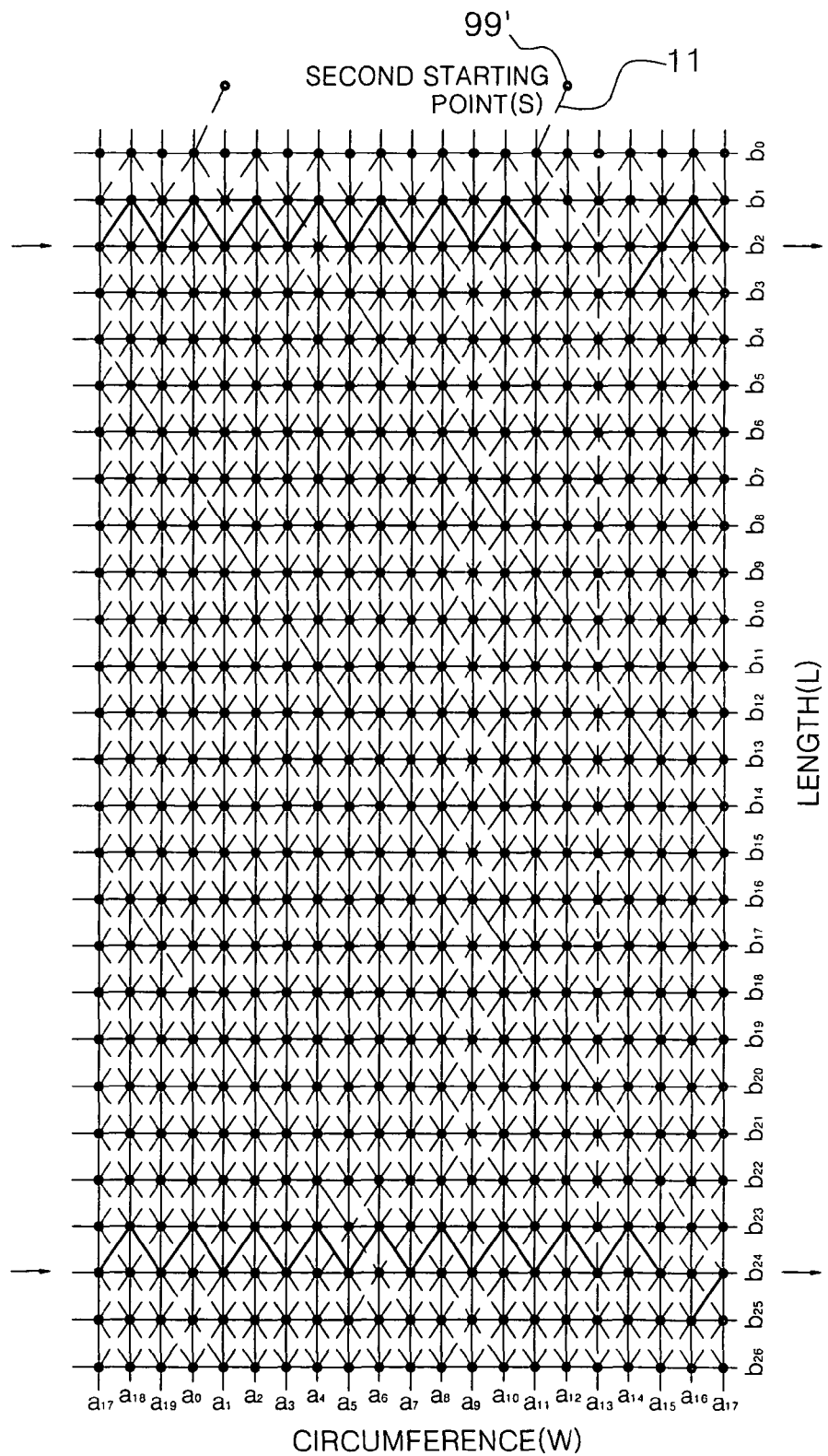

Turning to FIGS. 4c and 4d, the second wire 11 is extended upwardly from the lowermost zigzag part and then runs in zigzag along a circumferential direction of the cylinder 110 in such a manner as to form a plurality of middle cylindrical zigzag parts lying one above another in between the length dividing lines b25 through b1, as depicted in thick solid lines and thin dotted lines. The middle zigzag parts are interlocked with the part of the second wire 11 at the fifth secondary transition point a19b24 and also at the second secondary transition point a13b2. The number of the middle cylindrical zigzag parts is not subjected to any restriction and therefore may be changed depending on the length of the self-extendable stent 80 to be fabricated.

Figure 4E:
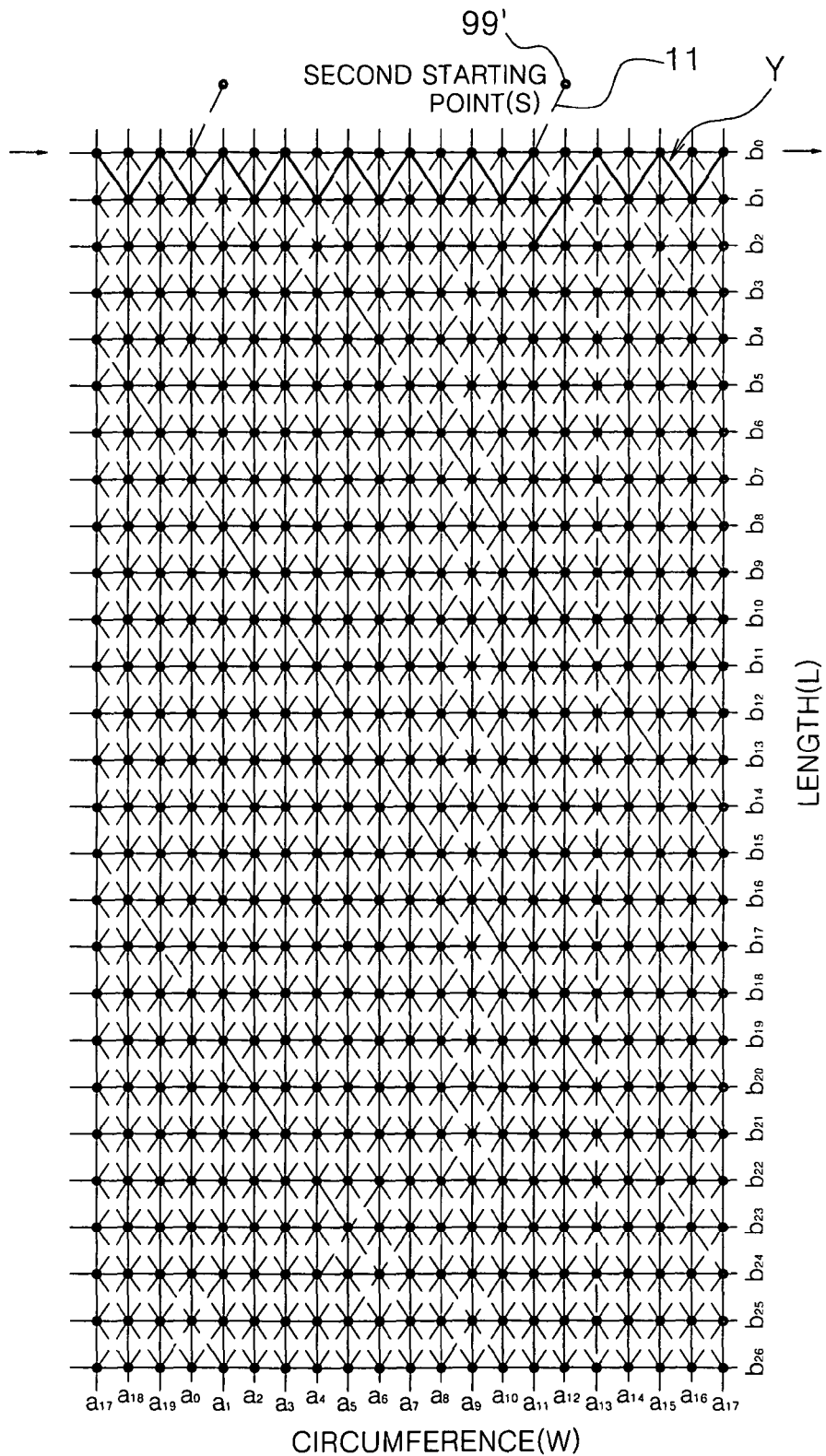

Referring to FIG. 4e, the second wire 11 is extended upwardly from the uppermost one of the middle zigzag parts and then runs in zigzag along a circumferential direction of the cylinder 110 in such a manner as to form an uppermost cylindrical zigzag part as depicted in thick solid lines. The uppermost cylindrical zigzag part is interlocked with the part of the second wire 11 at the third secondary transition point a14b1. The distal end of the first wire 11 is bonded to itself at the first primary transition point a11b0 in the vicinity of the second top starting point S. The bonding task is conducted by means of, e.g., a collapsible sleeve 200, as illustrated in FIG. 5 or by welding.

In this regard, the lowermost, middle and uppermost zigzag parts of the second wire 11 are joined to one another by secondary connecting wire parts each extending the first diagonal length 2ℓ between the adjoining zigzag parts in a diagonally upward direction.

As illustrated in FIG. 6a, the lowermost, middle and uppermost zigzag parts of the second wire 11 are interlocked with one another at interlocking portions 70 and disposed with respect to those of the first wire 10 in such a manner as to divide the rhombic spaces 20 formed by the first wire 10 into four small rhombic spaces, thereby completing the secondary stent member Y of the self-extendable stent 80. The auxiliary weaving grooves 130' provide wire moving passages, thus making it easier to conduct the task of interlocking the zigzag parts of the second wire 11.

It should be appreciated that the second wire 11 is not interlocked with itself at the downward extension part 75 that runs from the top to the bottom of the self-extendable stent 80 but interlocked with itself when it extends upwardly through the lowermost, middle and uppermost zigzag parts. The secondary stent member Y thus fabricated can be diametrically contracted within a predetermined extent, as shown in FIG. 6b, but undue longitudinal contraction or extension of the secondary stent member Y is prevented due to the presence of the downward extension part 75.

Every other projecting pin 120, which was not used in fabricating the first stent member X, is used in the process of fabricating the secondary stent member Y with the second wire 11.

At the time of fabricating the secondary stent member Y, the second wire 11 of the secondary stent member Y is arranged to intersect the first wire 10 of the primary stent member X at a multiplicity of intersection points 70. Furthermore, the first wire 10 and the second wire 11 are woven with each other in a plain weave pattern, namely, in such a manner that the second wire 11 passes alternately below and above the first wire 10 at the intersection points 70. Thus, the first and second stent members X and Y are prevented from being separated from each other.

The self-extendable stent 80 is completed by severing the remaining portions of the proximal and distal ends of the first and second wires 10 and 11, removing the projecting pins 120 from the base jig 100, separating the hollow cylindrical wire-woven body Z comprised of the first wire 10 and the second wire 11 from the base jig 100, and having the wire-woven body Z memorize its original shape through a heat treatment process.

The heat treatment process is carried out by, after fabrication of the wire-woven body Z, allowing the wire-woven body Z to memorize its original shape at a temperature at which the wire-woven body Z does not lose its elasticity. Specifically, the heat treatment process is preferably performed at a temperature ranging from 350 to 600° C. for 8 to 30 minutes.

As previously set forth, the self-expandable stent 80 of the present invention is fabricated using a super-elastic shape memory alloy wire having a diameter in the range of 0.1 to 0.5 mm. In case of the super-elastic shape memory alloy wire having a diameter smaller than or equal to 0.1 mm, the intrinsic elasticity of the wire becomes very low to such an extent that the stenosal portion cannot be sufficiently expanded by the self-extendable stent. In contrast, in the event of the super-elastic shape memory alloy wire having a diameter greater than 0.5 mm, the wire-woven body Z fails to have rhombic spaces of sufficiently great size, thus making it difficult to sufficiently reduce the volume of the wire-woven body Z.

The self-expandable shape memory alloy stent 80 fabricated by the afore-mentioned method includes first and second wires 10 and 11 woven each other against any separation.

The first wire 10 of the self-extendable stent 80 is made of a super-elastic shape memory alloy. When the self-extendable stent 80 is placed upright, the first wire 10 extends downwardly from a first top starting point to a first primary transition point disposed at an uppermost position of the stent 80 and then diagonally downwardly extends from the first primary transition point to a second primary transition point by a first diagonal length 2ℓ, where the ℓ denotes the distance between two diagonally neighboring transition points. Then, the first wire 10 extends diagonally upwardly from the second primary transition point to a third primary transition point by a second diagonal length l one half time smaller than the first diagonal length 2l and diagonally downwardly extends from the third primary transition point to a fourth primary transition point by a third diagonal length which is multiple times, e.g., 24 times, greater than the second diagonal length ℓ. The first wire 10 extends diagonally upwardly from the fourth primary transition point to a fifth primary transition point by the second diagonal length l and then diagonally downwardly extends by the first diagonal length 2ℓ from the fifth primary transition point to a sixth primary transition point disposed at a lowermost position of the stent 80.

This creates a downward extension part 75 (see FIG. 6a) which extends between the first primary transition point disposed at an uppermost position of the stent 80 and the sixth primary transition point disposed at a lowermost position of the stent 80. The downward extension part 75 serves to restrain the longitudinal contraction or extension, i.e., the length variation of the stent 80.

Subsequently, the first wire 10 extends in zigzag from the sixth primary transition point along a circumferential direction of the stent 80 to form a lowermost cylindrical zigzag part. The first wire 10 extends upwardly from the lowermost zigzag part in such a manner as to form a plurality of middle cylindrical zigzag parts and an uppermost cylindrical zigzag part. The lowermost, middle and uppermost zigzag parts are placed one above another along the length of the stent 80. The distal end of the first wire 10 is bonded to itself in the vicinity of the first top starting point.

In this regard, the lowermost, middle and uppermost zigzag parts of the first wire 10 are joined to one another by primary connecting wire parts each extending the first diagonal length 2ℓ between the adjoining zigzag parts in a diagonally upward direction.

As illustrated in FIG. 6a, the lowermost, middle and uppermost zigzag parts of the first wire 10 are interlocked with one another at interlocking portions 60 to leave a plurality of rhombic spaces 20 therebetween. It should be appreciated that the first wire 10 is not interlocked with itself at the downward extension part 75 that runs from the top to the bottom of the self-extendable stent 80 but interlocked with itself when it extends upwardly through the lowermost, middle and uppermost zigzag parts.

Just like the first wire 10 noted above, the second wire 11 of the self-extendable stent 80 is made of a super-elastic shape memory alloy. When the self-extendable stent 80 is placed upright, the second wire 11 extends downwardly from a second top starting point lying diametrically opposite from the first top starting point to a first secondary transition point disposed at an uppermost position of the stent 80, and then diagonally downwardly extends from the first secondary transition point to a second secondary transition point by a first diagonal length 2ℓ, where the ℓ denotes the distance between two diagonally neighboring transition points. Then, the second wire 11 extends diagonally upwardly from the second secondary transition point to a third secondary transition point by a second diagonal length ℓ one half time smaller than the first diagonal length 2ℓ and diagonally downwardly extends from the third secondary transition point to a fourth secondary transition point by a third diagonal length which is multiple times, e.g., 24 times, greater than the second diagonal length ℓ. The second wire 11 extends diagonally upwardly from the fourth secondary transition point to a fifth secondary transition point by the second diagonal length 1 and then diagonally downwardly extends by the first diagonal length 2ℓ from the fifth secondary transition point to a sixth secondary transition point disposed at a lowermost position of the stent 80.

This creates a downward extension part 75 (see FIG. 6a) which extends between the first secondary transition point disposed at an uppermost position of the stent 80 and the sixth secondary transition point disposed at a lowermost position of the stent 80. The downward extension part 75 serves to restrain the longitudinal contraction or extension, i.e., the length variation of the stent 80.

Subsequently, the second wire 11 extends in zigzag from the sixth secondary transition point along a circumferential direction of the stent 80 to form a lowermost cylindrical zigzag part. The second wire 11 extends upwardly from the lowermost zigzag part in such a manner as to form a plurality of middle cylindrical zigzag parts and an uppermost cylindrical zigzag part. The lowermost, middle and uppermost zigzag parts are placed one above another along the length of the stent 80. The distal end of the second wire 11 is bonded to itself in the vicinity of the second top starting point.

In this regard, the lowermost, middle and uppermost zigzag parts of the second wire 11 are joined to one another by secondary connecting wire parts each extending the first diagonal length 2ℓ between the adjoining zigzag parts in a diagonally upward direction.

As illustrated in FIG. 6a, the lowermost, middle and uppermost zigzag parts of the second wire 11 are interlocked with one another at interlocking portions 60 to leave a plurality of rhombic spaces 20 therebetween. It should be appreciated that the second wire 11 is not interlocked with itself at the downward extension part 75 that runs from the top to the bottom of the self-extendable stent 80 but interlocked with itself when it extends upwardly through the lowermost, middle and uppermost zigzag parts.

The second wire 11 is arranged to intersect the first wire 10 at a multiplicity of intersection points 70. Furthermore, the first wire 10 and the second wire 11 are woven with each other in a plain weave pattern, namely, in such a manner that the second wire 11 passes alternately below and above the first wire 10 at the intersection points 70. Thus, the first and second wires 10 and 11 are prevented from being separated from each other.

Figure 7:
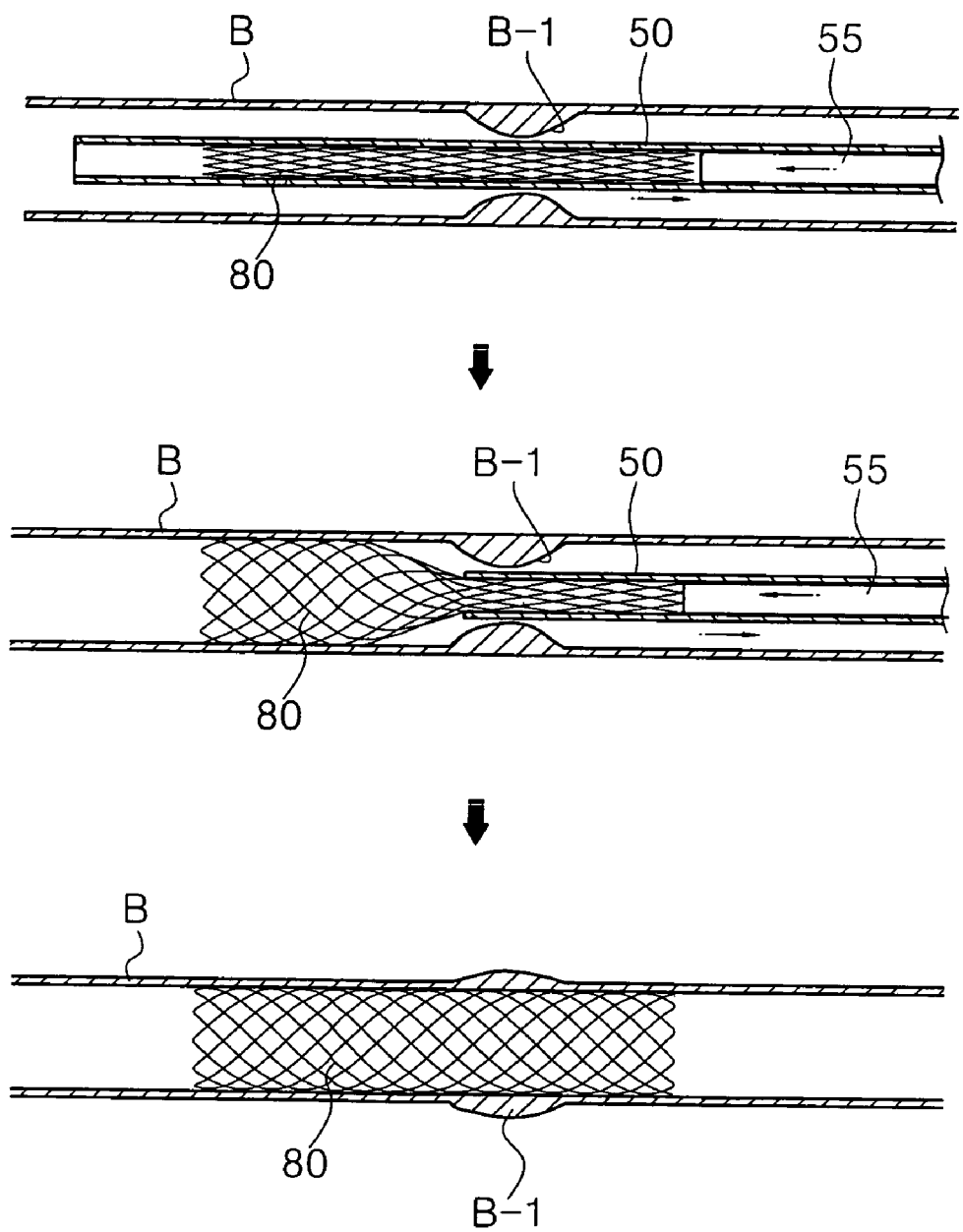
FIG. 7 is a conceptual view illustrating a process of installing the stent of the present invention into a blood vessel of a living body.

Referring now to FIG. 7, when in use, the self-extendable stent 80 is inserted into a target stenosal portion B-1 by reducing the diameter thereof with the collapse of the rhombic spaces 20, loading it within a guide tube 50, bringing the guide tube 50 to the stenosal portion B-1 through a blood vessel or the like, and then unloading it from the guide tube 50 through the use of a pusher catheter 55. This allows the self-extendable stent 80 to be expanded into its original shape whereby the passage of the stenosal portion B-1 can be enlarged by the expanding action of the self-extendable stent 80.

Figure 8:
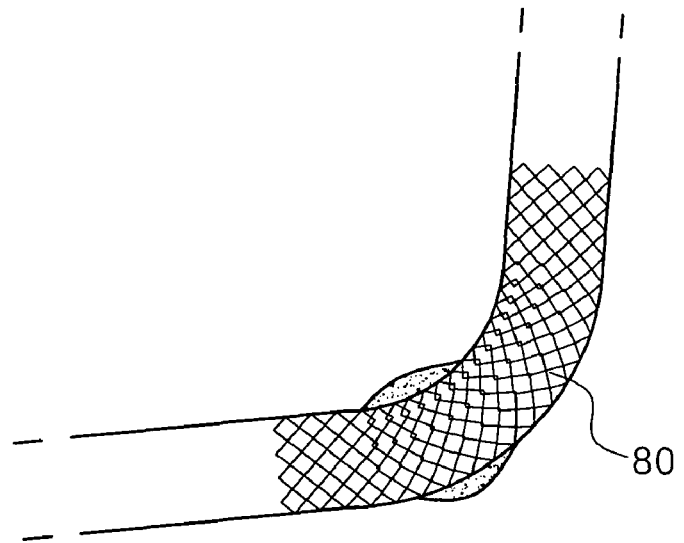
FIGS. 8 and 9 are state-of-use views of the stent in accordance with the present invention.
Figure 9:
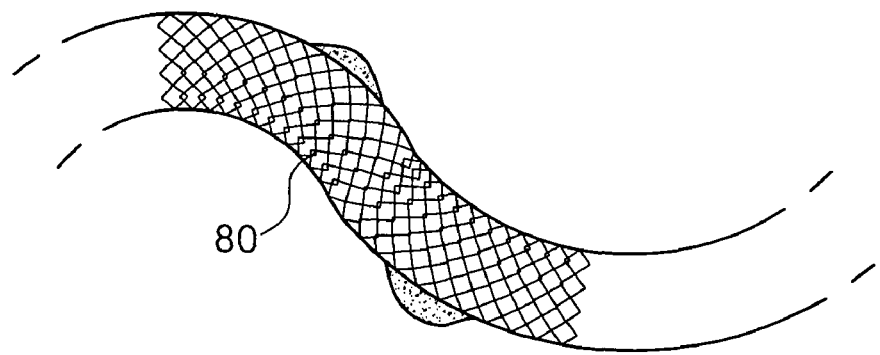

In particular, thanks to the combination of the interlocking portions 60 and the downward extension portion 75 (see FIGS. 6a and 6b), the self-extendable stent 80 of the present invention has an ability to flexibly conform to and maintain the shape of passage of the stenosal portion, whether straight (horizontal or vertical) or winding, as illustrated in FIGS. 8 and 9. Thus, the self-extendable stent 80 can minimize unwanted deformation of the stenosal portion and can effectively expand the stenosal portion by preventing any inadvertent length variation, such as longitudinal contraction and extension, in the process of installing, while maximizing its elasticity in a circumferential direction.

Although a preferred embodiment of the present invention has been described hereinabove, it will be apparent to those skilled in the art that various changes or modifications may be made thereto within the scope of the invention defined by the appended claims.

What is claimed is:

1. A self-expandable shape memory alloy stent comprising:
   a first wire made of a super-elastic shape memory alloy, the first wire extending downwardly from a first top starting point to a first primary transition point disposed at an uppermost position of the stent, diagonally downwardly extending from the first primary transition point to a second primary transition point by a first diagonal length $2\ell$, diagonally upwardly extending from the second primary transition point to a third primary transition point by a second diagonal length $\ell$, diagonally downwardly extending from the third primary transition point to a fourth primary transition point by a third diagonal length $24\ell$ without interlocking with itself, diagonally upwardly extending from the fourth primary transition point to a fifth primary transition point by the second diagonal length, and then diagonally downwardly extending by the first diagonal length from the fifth primary transition point to a sixth primary transition point disposed at a lowermost position of the stent, the first wire extending in zigzag from the sixth primary transition point along a circumferential direction of the stent to form a lowermost cylindrical zigzag part, the first wire extending upwardly from the lowermost zigzag part in such a manner as to form a plurality of middle cylindrical zigzag parts and an uppermost cylindrical zigzag part, the lowermost, middle and uppermost zigzag parts being interlocked with one another to leave a plurality of rhombic spaces therebetween; and
   a second wire made of a super-elastic shape memory alloy, the second wire extending downwardly from a second top starting point to a first secondary transition point disposed at an uppermost position of the stent, diagonally downwardly extending from the first secondary transition point to a second secondary transition point by a first diagonal length $2\ell$, diagonally upwardly extending from the second secondary transition point to a third secondary transition point by a second diagonal length $\ell$, diagonally downwardly extending from the third secondary transition point to a fourth secondary transition point by a third diagonal length $24\ell$, diagonally upwardly extending from the fourth secondary transition point to a fifth secondary transition point by the second diagonal length, and then diagonally downwardly extending by the first diagonal length from the fifth secondary transition point to a sixth secondary transition point disposed at a lowermost position of the stent, the second wire extending in zigzag from the sixth secondary transition point along a circumferential direction of the stent to form a lowermost cylindrical zigzag part, the second wire extending upwardly from the lowermost zigzag part in such a manner as to form a plurality of middle cylindrical zigzag parts and an uppermost cylindrical zigzag part, the lowermost, middle and uppermost zigzag parts of the second wire being interlocked with one another to leave a plurality of rhombic spaces therebetween,
   wherein the second wire is arranged to intersect the first wire at a multiplicity of intersection points and wherein the first wire and the second wire are woven with each other in such a manner that the second wire passes alternately below and above the first wire at the intersection points, and
   wherein the lowermost, middle, and uppermost zigzag parts of each of the first and the second wire are joined to one another by primary and secondary connecting wire parts each extending the first diagonal length between the adjoining zigzag parts in a diagonally upwardly direction.

2. The self-expandable shape memory alloy stent as recited in claim 1, wherein the first top starting point from which the first wire begins to extend is diametrically opposite to the second top starting point from which the second wire begins to extend.

3. The self-expandable shape memory alloy stent as recited in claim 1, wherein the first wire has an end point fixedly secured to the first wire in the vicinity of the first top starting point, and the second wire has an end point fixedly secured to the second wire in the vicinity of the second top starting point.

4. A self-expandable shape memory alloy stent comprising:
   a first wire made of a super-elastic shape memory alloy, the first wire extending downwardly from a first top starting point to a first primary transition point disposed at an uppermost position of the stent, diagonally downwardly extending from the first primary transition point to a second primary transition point by a first diagonal length $2\ell$, diagonally upwardly extending from the second primary transition point to a third primary transition point by a second diagonal length $\ell$, diagonally downwardly extending from the third primary transition point to a fourth primary transition point by a third diagonal length $24\ell$ without interlocking with itself, diagonally upwardly extending from the fourth primary transition point to a fifth primary transition point by the second diagonal length, and then diagonally downwardly extending by the first diagonal length from the fifth primary transition point to a sixth primary transition point disposed at a lowermost position of the stent, the first wire extending in zigzag from the sixth primary transition point along a circumferential direction of the stent to form a lowermost cylindrical zigzag part, the first wire extending upwardly from the lowermost zigzag part in such a manner as to form a plurality of middle cylindrical zigzag parts and an uppermost cylindrical zigzag part, the lowermost, middle and uppermost zigzag parts being interlocked with one another to leave a plurality of rhombic spaces therebetween; and a second wire made of a super-elastic shape memory alloy, the second wire extending downwardly from a second top starting point to a first secondary transition point disposed at an uppermost position of the stent, diagonally downwardly extending from the first secondary transition point to a second secondary transition point by a first diagonal length $2\ell$, diagonally upwardly extending from the second secondary transition point to a third secondary transition point by a second diagonal length $\ell$, diagonally downwardly extending from the third secondary transition point to a fourth secondary transition point by a third diagonal length $24\ell$ without interlocking with itself, diagonally upwardly extending from the fourth secondary transition point to a fifth secondary transition point by the second diagonal length, and then diagonally downwardly extending by the first diagonal length from the fifth secondary transition point to a sixth secondary transition point disposed at a lowermost position of the stent, the second wire extending in zigzag from the sixth secondary transition point along a circumferential direction of the stent to form a lowermost cylindrical zigzag part, the second wire extending upwardly from the lowermost zigzag part in such a manner as to form a plurality of middle cylindrical zigzag parts and an uppermost cylindrical zigzag part, the lowermost, middle and uppermost zigzag parts of the second wire being interlocked with one another to leave a plurality of rhombic spaces therebetween, wherein the second wire is arranged to intersect the first wire at a multiplicity of intersection points, wherein the first wire and the second wire are woven with each other in such a manner that the second wire passes alternately below and above the first wire at the intersection points, and wherein the lowermost, middle, and uppermost zigzag parts of each of the first and the second wire are joined to one another by primary and secondary connecting wire parts each extending the first diagonal length between the adjoining zigzag parts in a diagonally upwardly direction.

* * * * *